United States Patent [19]
Luce

[11] Patent Number: 5,779,633
[45] Date of Patent: *Jul. 14, 1998

[54] TONOMETER AIR PULSE GENERATOR

[75] Inventor: David A. Luce, Clarence Center, N.Y.

[73] Assignee: Leica Inc., Depew, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 659,704

[22] Filed: Jun. 10, 1996

[51] Int. Cl.$^6$ .................................... A61B 3/16
[52] U.S. Cl. ................. 600/398; 600/401; 600/405
[58] Field of Search ................. 128/645, 648, 128/649, 652; 417/412, 413.1, 443, 445, 446, 496, 553, 562; 600/398, 401, 402, 405

[56] References Cited

U.S. PATENT DOCUMENTS

| 4,770,181 | 9/1988 | Tomoda | 128/648 |
| 4,817,620 | 4/1989 | Katsuragi et al. | 128/648 |
| 5,048,526 | 9/1991 | Tomoda | 128/648 |
| 5,165,408 | 11/1992 | Tomoda | 128/648 |
| 5,279,300 | 1/1994 | Miwa et al. | |

Primary Examiner—Jennifer Bahr
Assistant Examiner—Bryan K. Yarnell
Attorney, Agent, or Firm—Bean, Kauffman & Snyder

[57] ABSTRACT

An air pulse generator for a non-contact tonometer comprises a bi-directional linear motor drivably connected to a compression mechanism and responsive to an applanation signal for reducing unnecessary air pulse energy delivered to an eye. Upon receiving the applanation signal from an applanation detector, a motor controller reverses current flow in the coil of the motor to create a reverse electromagnetic force to stop generation of the air pulse. In a first embodiment, the linear motor includes a moving permanent magnet armature for reversibly driving the compression mechanism, while in a second embodiment, the linear motor includes a moving coil for reversibly driving the compression mechanism.

19 Claims, 7 Drawing Sheets

TONOMETER AIR PULSE GENERATOR

BACKGROUND

A. Field of the Invention

The present invention relates generally to "air puff" non-contact tonometers (NCTs) used for measuring the intra-ocular pressure of a patient's eye, and more particularly to a novel air pulse generator for an NCT utilizing bi-directional piston drive means responsive to an applanation signal to stop air pulse generation and thus minimize unnecessary air pulse force delivered to the eye.

B. Description of the Prior Art

NCTs have been in commercial use for more than twenty years. NCTs produce an air pulse which flattens a portion of the cornea, an event known in the art as "applanation", and simultaneously measure a parameter, for example a time duration or a plenum air pressure, which can be correlated with the pressure exerted on the eye. In a large number of prior art NCTs, a determination of the moment of applanation is used to determine the instantaneous plenum pressure at such moment, which in turn is used to determine the correlative intra-ocular pressure measurement.

One important factor in performing the air pulse measurement is the amount of air pulse energy delivered to the eye to make such a measurement. It is intuitively clear that the amount of air pulse energy required to applanate the eye increases as the intra-ocular pressure increases. However, in the current state of the art, much of the air pulse energy delivered to the eye is not just the amount of energy required to applanate the eye, but a sum of the energy required to applanate the eye, the kinetic energy acquired by the air pump mechanism(s) during its acceleration to the velocity required to develop an air velocity adequate to cause applanation, and the energy acquired by the compressed air contained in the plenum. This additional air pulse energy results in a substantial "extra puff" which causes discomfort to the patient.

Minimizing unnecessary air pulse energy is an important product feature, as discussed in the recently issued U.S. Pat. No. 5,279,300, which discloses a method whereby initial intra-ocular pressure measurement values are used to limit the time duration of the air pulse generation on subsequent measurements. This approach, however, does not limit the air pulse energy on the initial measurement. Since it is common to take only a single measurement, this approach does not contribute any relief to the majority of patients who are subjected to only one measurement.

Originally, the vast majority of NCTs sold used a rotary solenoid in cooperation with a piston mechanism to generate and deliver an air pulse to the eye. Commercially available tonometers typically determine the moment of applanation using optical detection means, for example by measuring peak reflection of obliquely angled source light by the cornea to an area detector on an opposite side of the eye from the light source. The rotary solenoid was originally selected because it provided a linear air pressure ramp versus time, thereby allowing correlation of intra-ocular pressure to time.

During the past twenty years, electronic technology has improved, thereby permitting the use of pressure transducers positioned in the plenum chamber of the piston mechanism to directly measure air pressure and consequently eliminating the need to rely on time and a linear air pressure ramp for determination of intra-ocular pressure. Nevertheless, manufacturers have continued to use rotary solenoids, even though the majority of non-contact tonometers currently produced use pressure transducers positioned in the plenum chamber.

FIG. 1 shows a prior art air pulse generator 10 used in a non-contact tonometer (not shown). Air pulse generator 10 is typical of prior art constructions in that it includes a housing 12 and compression means in the form of a piston 14 cooperating to define an upper plenum chamber 16 and lower chamber 17 containing air or other fluid, and an air discharge tube 18 having an inlet end 20 in communication with plenum chamber 16 and an outlet end 22. Air discharge tube 18 is normally arranged to extend horizontally, and is positionable along a test axis 6 with outlet end 22 proximate to an eye 2 of a patient for directing an air pulse at the eye.

In the prior art pulse generator, a rotary solenoid 24 is provided for driving piston 14 in a direction along piston axis 14A to linearly increase air pressure within plenum chamber 16, and thereby produce an air pulse discharged at outlet end 22 of air discharge tube 18. Solenoid 24 includes an armature 26 composed of a ferromagnetic material and operatively connected to piston rod 28. When the solenoid coil (not shown) is energized by solenoid drive circuit 30, electromagnetic force causes armature 26 to rotate in a clockwise direction, as shown in FIG. 1, to drive piston 14 along piston axis 14A. Notably, in keeping with the characteristics of a common solenoid, the forces developed on armature 26 are independent of the polarity of the magnetic field created by the current flowing through the solenoid coil, and thus the direction of motion of armature 26 and piston 14 is the same regardless of the direction of current flowing through the solenoid coil.

In the above-described prior art mechanism, the air pulse generation process is halted by stopping the flow of current in the solenoid coil, preferably immediately after applanation of the cornea is detected, and the piston is returned to its start position by a spring (not shown) for rotating solenoid armature 26 in a counter-clockwise direction. However, it is recognized that kinetic energy of the moving armature 26 and connected piston 14, and the potential energy stored in the compressed air in plenum chamber 16, continue to cause air flow subsequent to the de-energizing of the solenoid coil, resulting in an unnecessary and substantial extra puff energy beyond that required to cause applanation. FIG. 2 is a graph which illustrates the air pulse force versus time delivered to a rubber eye having an intraocular pressure of 15.6 mmHg. The impulse delivered to the eye, represented by the area under the force-time curve, is approximately 400% of that required to cause applanation.

It is known to use a bi-directional linear motor, rather than a rotary solenoid, to drive a piston of an NCT air pulse generator, as disclosed in U.S. Pat. Nos. 4,770,181 and 5,048,526. These patents teach that current flow in the motor coil may be reversed after the flow of air through an outlet is completed, and thus do not solve the problem of an "extra puff".

SUMMARY OF THE INVENTION

Therefore, it is an object of the present invention to reduce the air pulse energy applied to an eye for non-contact measurement of intra-ocular pressure.

It is another object of the present invention to use a bi-directional linear motor for generating an air pulse and stopping air pulse generation in response to an applanation signal.

It is a further object of the present invention to absorb the kinetic energy acquired by moving parts of an air pump mechanism and the energy stored in the compressed air during air pulse generation.

It is a further object of the present invention to reduce the kinetic energy acquired by moving parts of an air pump mechanism and the energy stored in the compressed air during air pulse generation.

In accordance with a first embodiment of the present invention, a permanent magnet armature of a linear d.c. motor is drivably coupled to a piston mechanism for generating an air pulse directed through an air discharge tube toward an eye of a patient to cause applanation of the cornea. A control circuit for the motor receives an applanation signal from an opto-electric applanation detection system and reverses the current flow through the motor coil in response to the signal, thereby creating a reverse electromagnetic force on the armature to stop piston motion almost instantly and substantially eliminate "extra puff" due to piston inertia. Alternatively, the motor control circuit may simply stop current flow in response to the applanation signal, whereby induced reverse current in the motor coil will provide electromagnetic braking force.

A second embodiment of the present invention differs from the first in that a moving coil linear motor, i.e. a loudspeaker voice coil, drives the piston in a reversible manner. Use of a moving coil, rather than a moving permanent magnet, is advantageous because it results in a decrease in system kinetic energy due to the lower mass of the coil relative to the permanent magnet. Further alternative constructions for reducing system kinetic energy include using an enlarged area piston, a diaphragm pump, or a bellows pump as air compression means.

A third embodiment of the present invention includes a fixed electromagnet in place of the fixed permanent magnet of the second embodiment.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
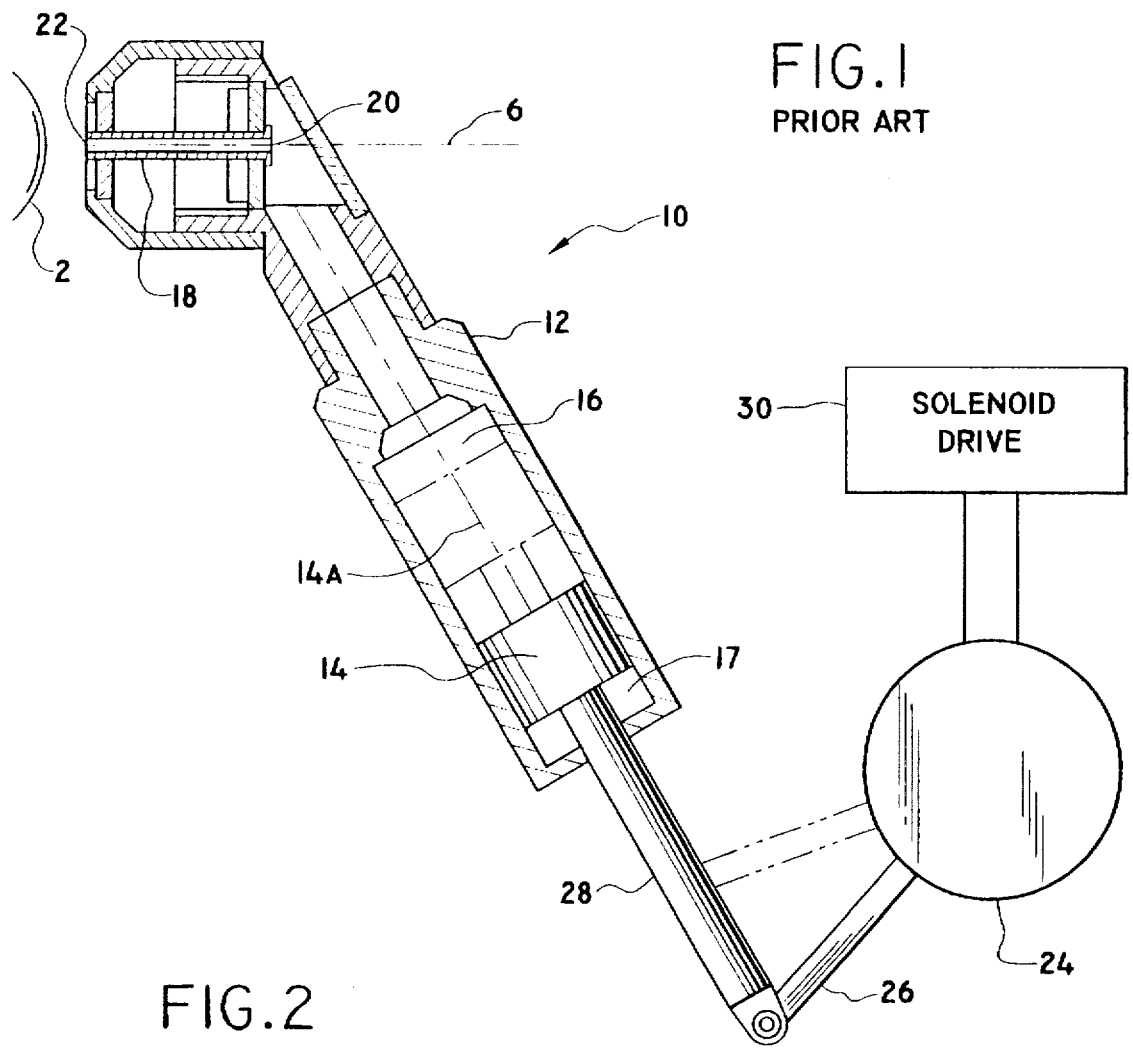
FIG. 1 is a cross-sectional view of a prior art air pulse generator utilizing a solenoid drive mechanism.
Figure 2:
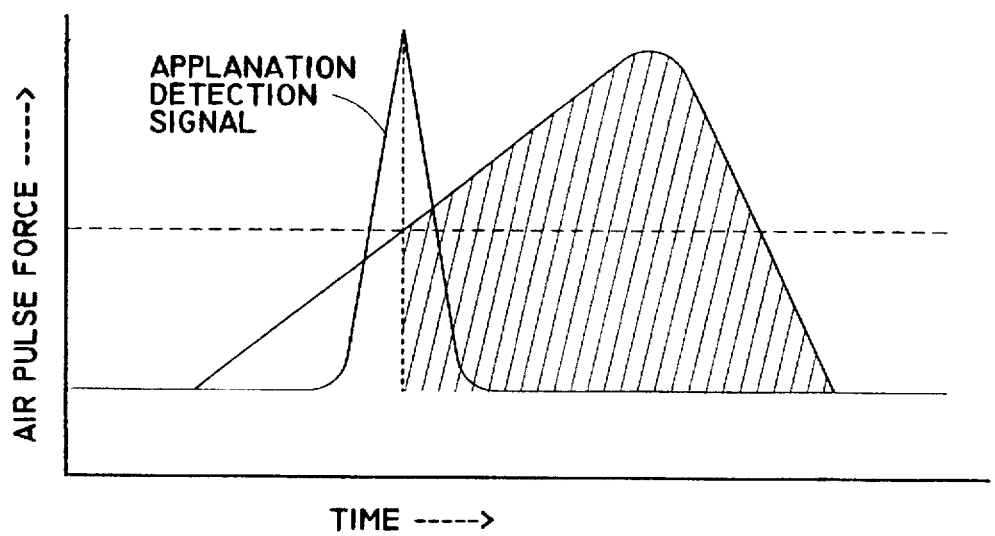
FIG. 2 is a graph of air pulse force as a function of time for a prior art air pulse generator of the type shown in FIG. 1, as tested on a rubber eye, with the applanation detection signal superimposed thereon.
Figure 3:
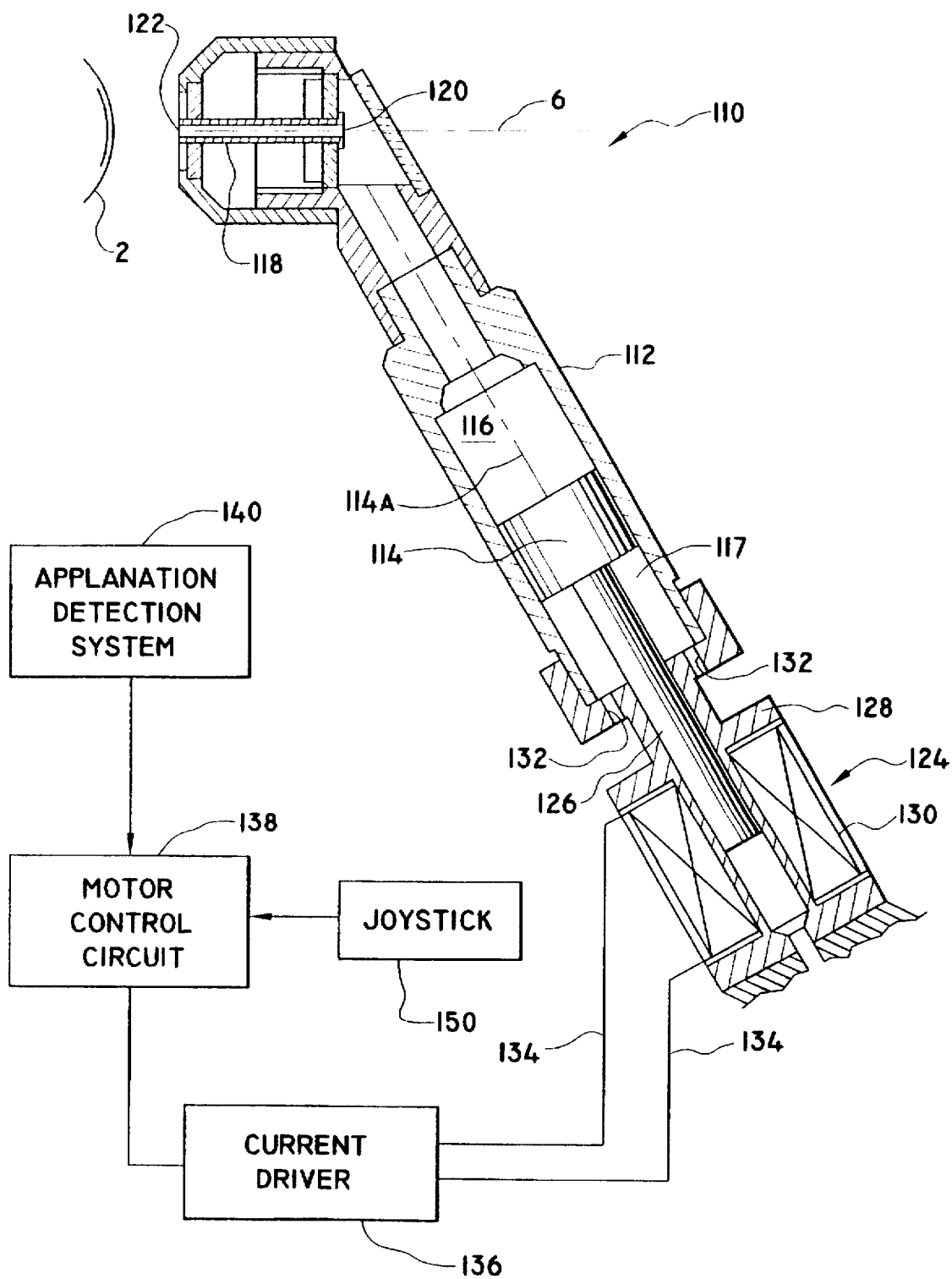
FIG. 3 is a cross-sectional view of an air pulse generator formed in accordance with a first embodiment of the present invention.

Referring now to FIG. 3, an air pulse generator formed in accordance with a first embodiment of the present invention is depicted in cross-section and generally designated as 110. Air pulse generator 110 is similar to the prior art mechanism of FIG. 1 in that it includes a housing 112 and a piston 114 cooperating to define an upper plenum chamber 116 and lower chamber 117 containing air, and an air discharge tube 118 having an inlet end 120 in communication with plenum chamber 116 and an outlet end 122. Air discharge tube 118 is alignable on horizontal test axis 6, with outlet end 122 proximate to eye 2.

In accordance with the present invention, a linear d.c. motor 124 is provided for successively forcing piston 114 in a first direction along piston axis 114A to increase air pressure within plenum chamber 116 and generate an air pulse, and then in a second direction opposite the first direction subsequent to applanation of the cornea to stop generation of the air pulse. Linear motor 124 includes a permanent magnet piston rod 126 axially movable within a bobbin 128 coaxially attached to housing 112, coil 130 wound on bobbin 128, and holes 132 formed in bobbin 128 to permit communication of lower chamber 117 with the atmosphere.

Figure 4:
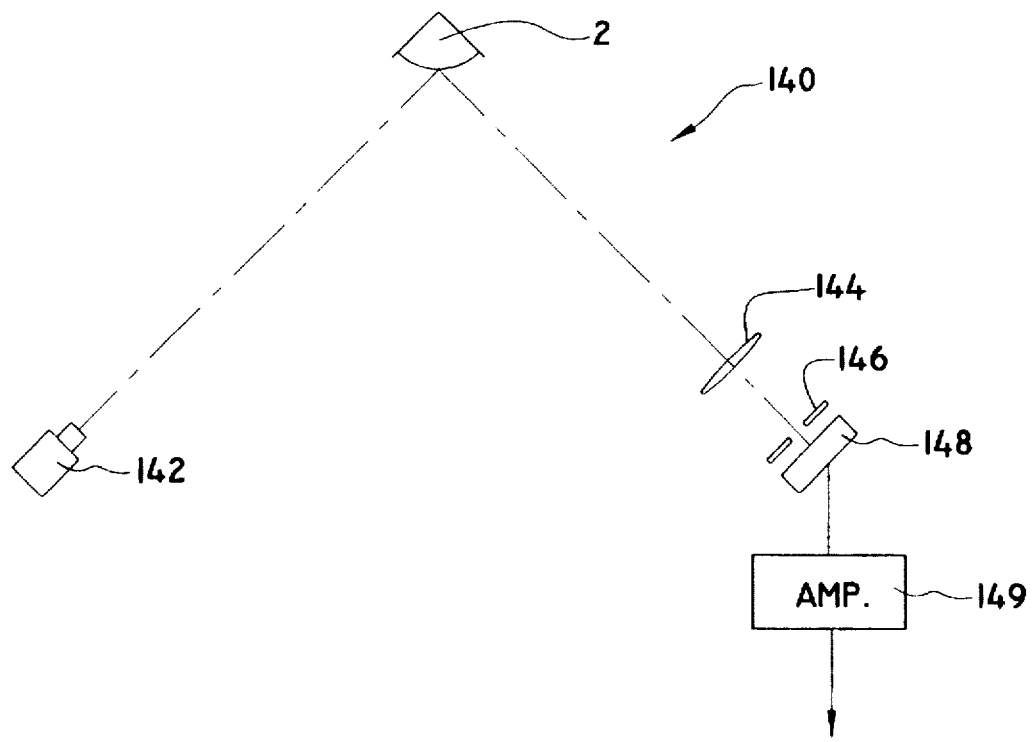
FIG. 4 is a schematic view of a prior art applanation detection system suitable for use in practicing the present invention.

Linear motor 124 is connected by leads 134 to a current driver 136 for energizing the linear motor. Current driver 136 is controlled by a motor control circuit 138, which is wired to receive an activation or "firing" signal from a joystick firing button 150 or other firing means, and an applanation signal from applanation detection means 140. Applanation detection means 140, shown schematically in FIG. 4, may be of a type used, for instance, in the XPERT® NCT manufactured by Reichert Ophthalmic Instruments, a division of Leica, Inc., assignee of the present application. Applanation detection means 140 is an opto-electronic system comprising an emitter 142 for directing an oblique, collimated, infra-red beam toward a corneal pole of eye 2 for reflection thereby, a collector lens 144 on an opposite side of the eye, a pinhole occluder 146 situated in the focal plane of collector lens 144, and an area detector 148 located adjacent pinhole occluder 146. Detector 148 measures a peak of reflected rays at the instant of applanation and passes an applanation detection signal to amplifier 149.

In operation, motor control circuit 138 responds to the firing signal by energizing coil 130 to produce a magnetic field whose polarity is in the same direction as that of permanent magnet piston rod 126, such that the piston rod moves in the first direction along axis 114A, generally upward as shown in FIG. 3, to generate an air pulse. Once applanation is detected by applanation detection means 140, an applanation signal is sent thereby to motor control circuit 138, which preferably responds by reversing the direction of current in coil 130, thereby reversing the polarity of the resulting magnetic field such that its poles are opposite in direction relative to the poles of permanent magnet piston rod 126. Consequently, a reversing electromagnetic force is produced which acts to stop the motion of piston 114 in the first direction, and which may be made sufficiently great to cause piston 114 to move in an opposite or second direction along axis 114A, generally downward in FIG. 3. Motor control circuit 138 may be designed to supply a very large reverse current for a very short time to stop the motion of piston 114 almost instantly.

Motor control circuit 138 may also be designed to short the current supply circuit to coil 130 upon receiving the applanation signal, rather than reverse the current in the coil. When the circuit is shorted in response to the applanation signal, a reverse current is induced in coil 130 by virtue of relative motion between permanent magnet piston rod 126 and coil 130 due to inertia of the moving piston mechanism.

As with the driven reverse current discussed above, the induced reverse current provides effective electrodynamic braking of the linear motor system.

Figure 5:
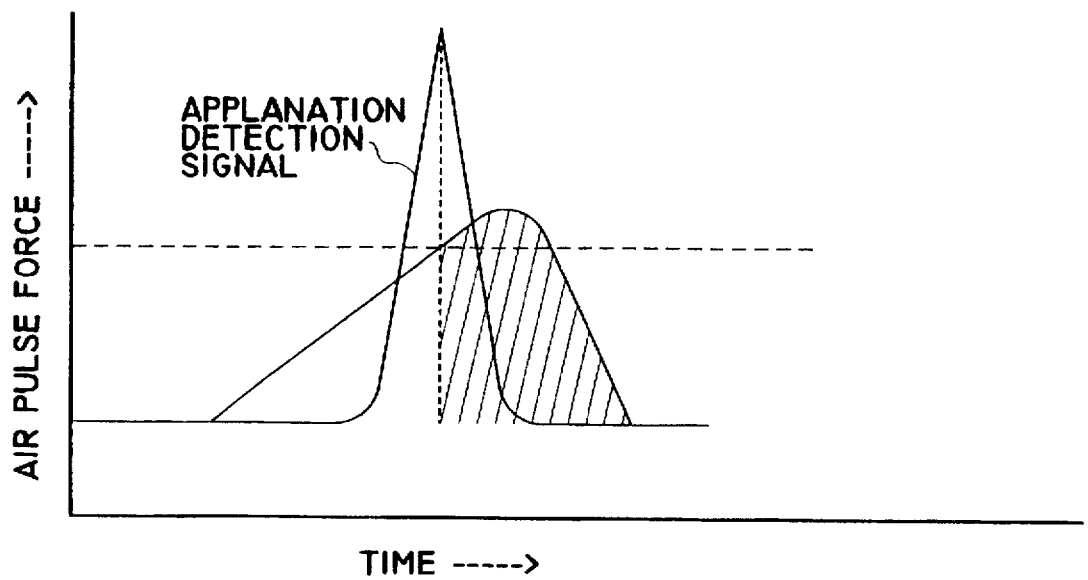
FIG. 5 is a graph of air pulse force as a function of time for the air pulse generator of FIG. 3, as tested on a rubber eye, with the applanation detection signal superimposed thereon.

Because the air pulse generator of the present invention applies force in a reverse direction immediately following applanation to stop the air pulse generation process, the impulse delivered to eye 2 subsequent to applanation is substantially reduced. An NCT utilizing an air pulse generator formed in accordance with the embodiment of FIG. 3 was tested using a rubber eye with an intra-ocular pressure of 15.6 mmHg, and a plot of air pulse force versus time is provided in FIG. 5. As will be apparent to those skilled in the art, the impulse delivered to the eye is approximately 150% of that required to cause applanation, which represents a substantial improvement over the prior art.

Figure 6:
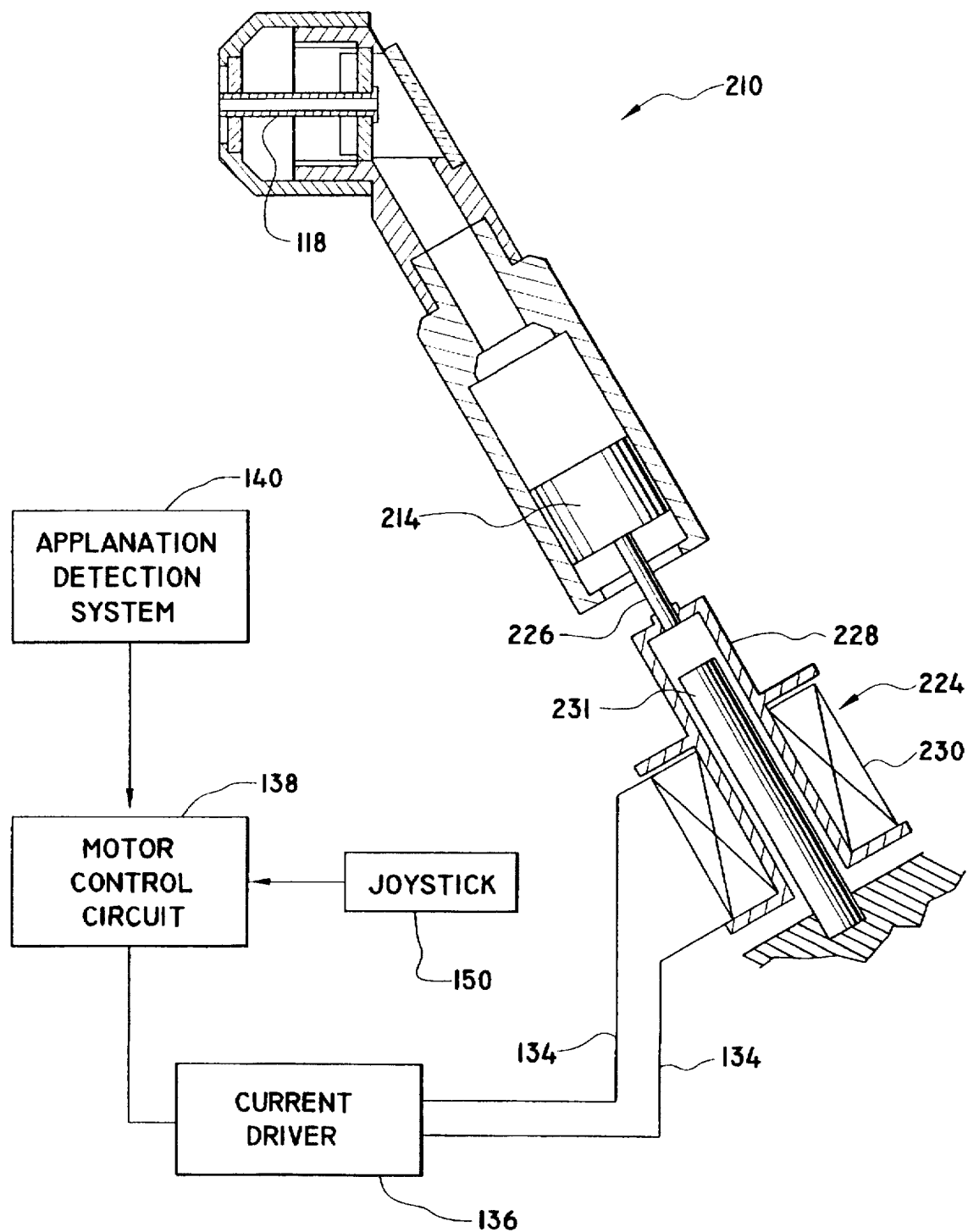
FIG. 6 is a cross-sectional view of an air pulse generator formed in accordance with a second embodiment of the present invention.

Referring now to FIG. 6, a second embodiment of the present invention is shown. An air pulse generator 210 having a piston 214 and a linear motor 224 differs from the first embodiment described above in that a lightweight piston rod 226 is connected to a moving voice coil 230 wound on a moving cylindrical bobbin 228, and a stationary permanent magnet 231 extends axially within bobbin 228. Current driver 136 is connected by wires 134 to voice coil 230 for energizing the coil. Like the first embodiment, the second embodiment includes motor control circuit 138 connected to receive an applanation signal from applanation detection means 140.

The second embodiment of FIG. 6 operates in a manner generally similar to the first embodiment, except that the motor coil moves and the permanent magnet remains in a fixed position. Thus, the second embodiment operates essentially according to the principle of a loudspeaker. Since the kinetic energy attributable to a linear motor equals $\frac{1}{2} mv^2$, where m is the mass of the moving "armature" and v is its velocity, the second embodiment is advantageous compared with the first embodiment because a relatively light voice coil moves instead of a relatively heavy permanent magnet, thereby helping to reduce the kinetic energy of the system and the "extra puff" resulting therefrom. A 4-½" diameter, 25 watt, 8 ohm impedance loudspeaker manufactured by CTS Corporation of Paducah, Ill. has been tested and found to generate a satisfactory pulse.

Figure 7:
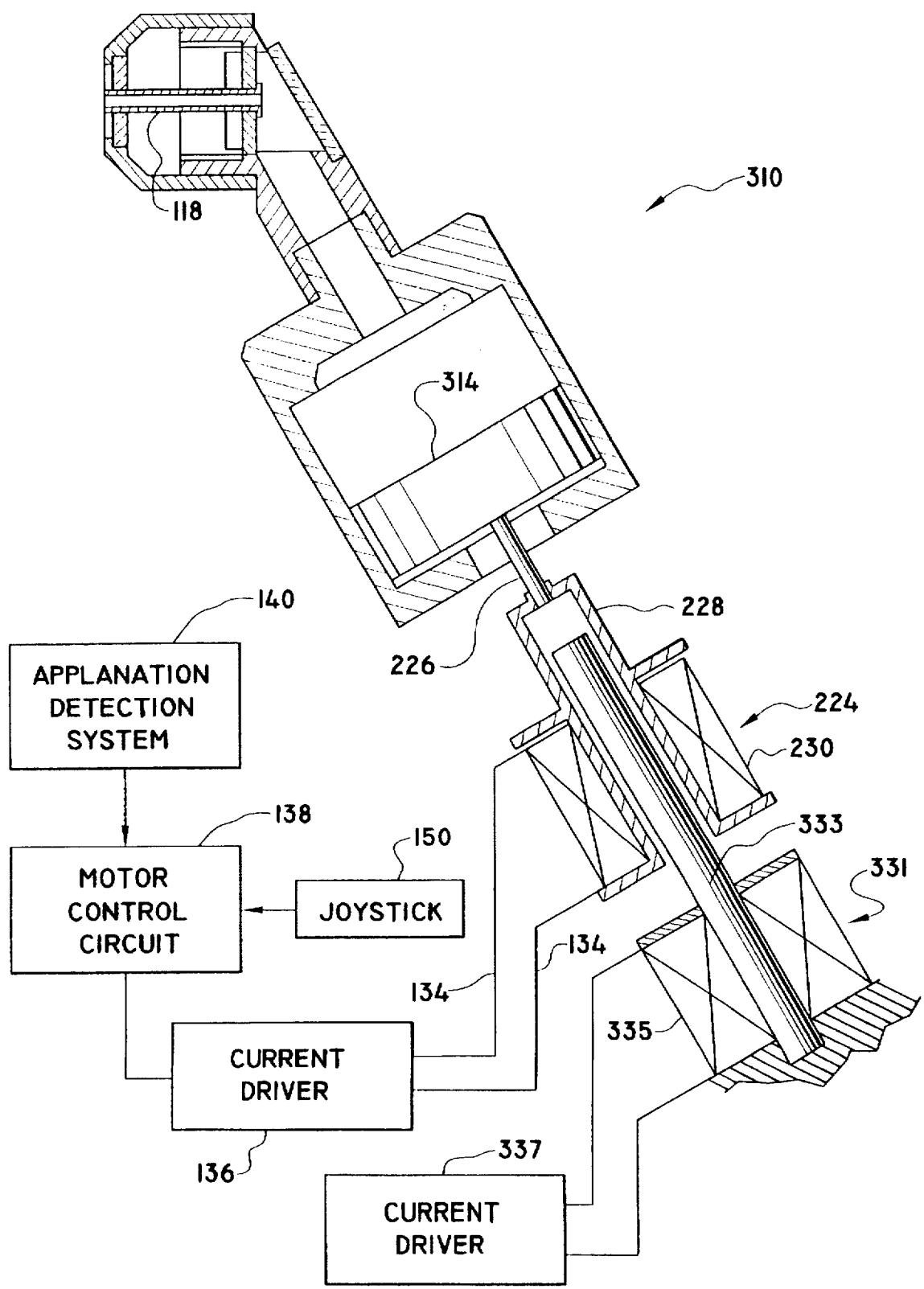
FIG. 7 is a cross-sectional view of an air pulse generator formed in accordance with a third embodiment of the present invention.

FIG. 7 shows a third embodiment air pulse generator of the present invention, generally designated as 310, which is substantially like the second embodiment described above, except that its motor utilizes an electromagnet 331 in place of the permanent magnet 231 of the second embodiment, and a piston 314 of the air pulse generator has an increased area relative to piston 214 of the second embodiment.

Electromagnet 331 includes an elongated cylindrical core 333 having a high magnetic permeability, and a surrounding coil 335 fixed at an end thereof opposite voice coil 230. Coil 335 is connected to a current driver 337 which causes current flow in coil 335 when power is supplied to the NCT, thereby creating a magnetic field equivalent to that of a permanent magnet while power is on. Electromagnet 331 is less expensive to manufacture than a permanent magnet, and permits control over the magnetic field through adjustment of current driver 337.

The increased area of piston 314 permits a corresponding decrease in piston velocity to impart the same velocity to a given volume of air. The mass of piston 314 is greater than that of piston 214, however the relatively slower velocity of piston 314 and voice coil 230 coupled thereto more than offsets the increase in mass, resulting in further reduction of overall system kinetic energy.

Figure 8:
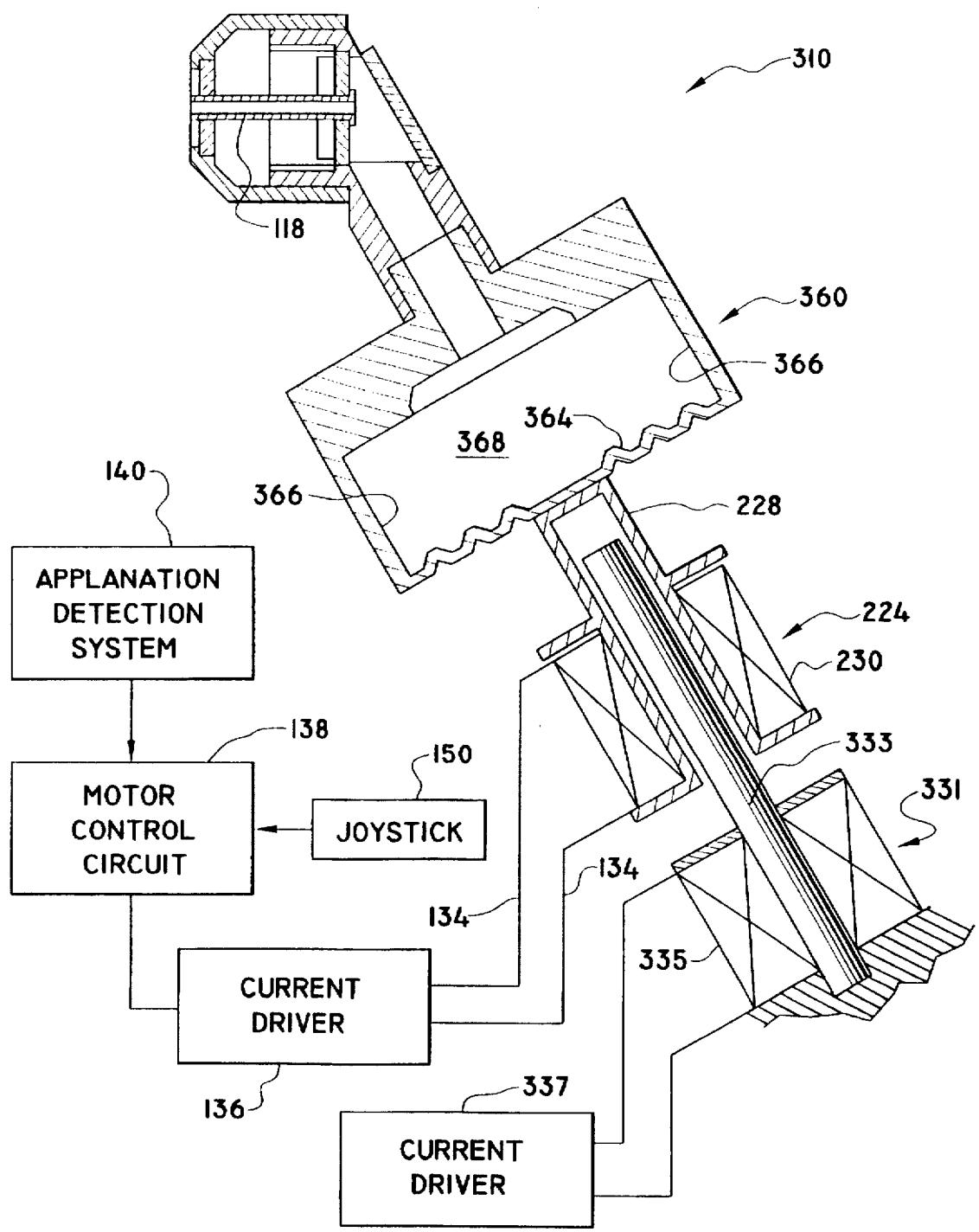
FIG. 8 is a cross-sectional view of an air pulse generator similar to that depicted in FIG. 7, except that the compression means thereof is a diaphragm pump.
Figure 9:
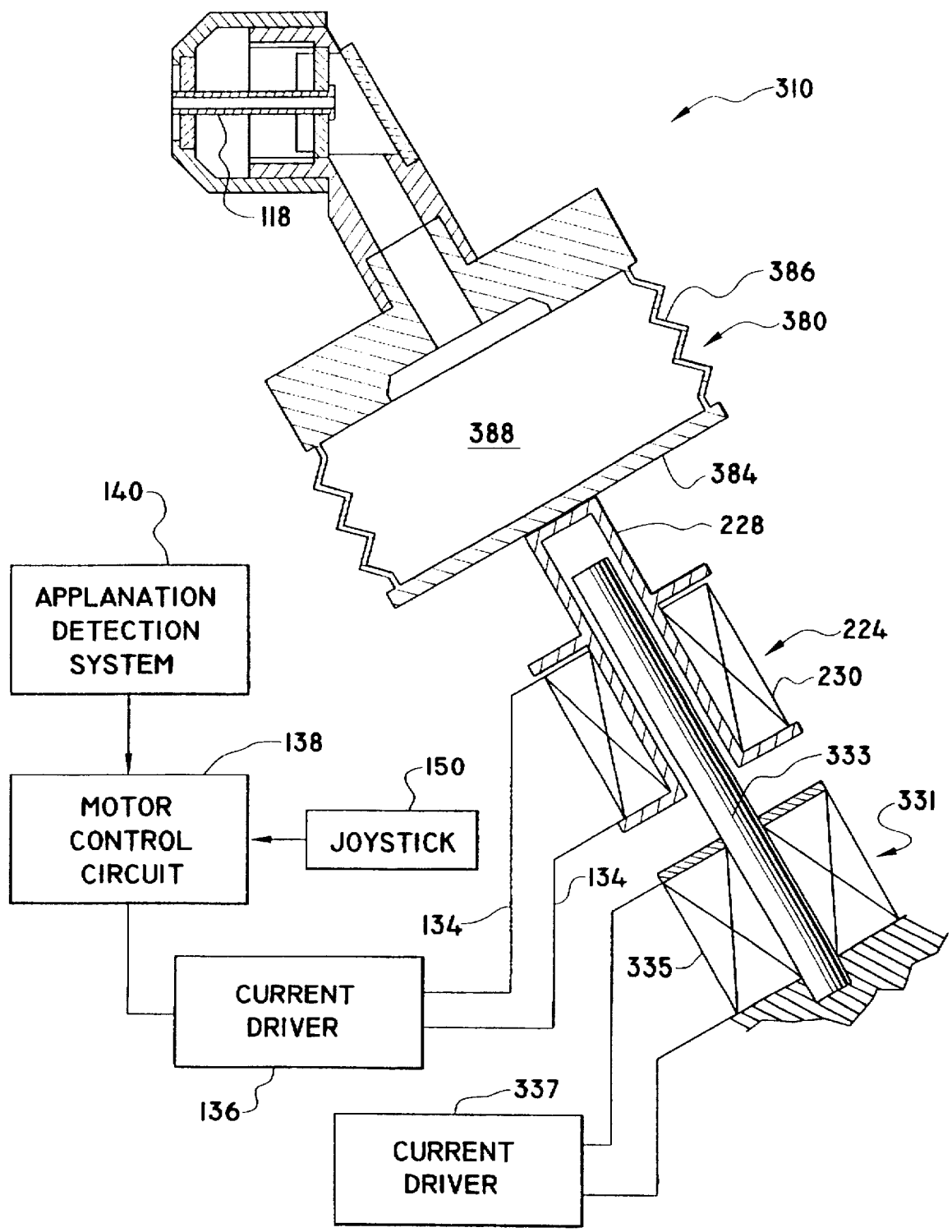
FIG. 9 is a cross-sectional view of an air pulse generator similar to that depicted in FIG. 7, except that the compression means thereof is a bellows pump.

Compression means may also be a flexible diaphragm pump 360 attached directly to moving bobbin 228, as shown in FIG. 8. Diaphragm pump 360 includes a flexible wall 364 cooperating with pump walls 366 to define a chamber 368 communicating with air discharge tube 118. A low cost, commercially available diaphragm pump may be used. As will be appreciated, diaphragm pump 360 has no friction generating parts, and chamber 368 has no leakage except through air discharge tube 118, which is of course desired. Furthermore, diaphragm pump 360 is easily constructed to have a large area and small motion, fulfilling the design considerations discussed above in relation to the increased-area piston of FIG. 7. Similar advantages may also be realized using a bellows pump 380 for air compression, as depicted in FIG. 9. Bellows pump 380 is coupled to linear motor 224 by attachment of moving bobbin 228 to end wall 384, and includes an axially compressible tube 386 defining a chamber 388 communicating with air discharge tube 118.

What is claimed is:

1. A non-contact tonometer for making a measurement of intraocular pressure of an eye, said non-contact tonometer having an outlet for directing an increasing velocity air pulse toward said eye and detecting means for generating a signal indicating applanation of the eye caused by said air pulse, which comprises:

compression means communicating with said outlet for generating said air pulse;

a motor drivably connected to said compression means;

energizing means connected to said motor for providing force to move said compression means in a first direction along an axis and produce said air pulse; and reversing means connected to said energizing means for providing force to stop generation of said air pulse directly in response to said signal generated during said measurement.

2. The non-contact tonometer according to claim 1, wherein said compression means includes a bellows pump.

3. The non-contact tonometer according to claim 1, wherein said compression means includes a diaphragm pump.

4. The non-contact tonometer according to claim 1, wherein said compression means includes a piston pump.

5. The non-contact tonometer according to claim 1, wherein said force to stop generation of said air pulse is sufficient to move said compression means in a second direction opposite said first direction.

6. The non-contact tonometer according to claim 5, wherein said compression means includes a bellows pump.

7. The non-contact tonometer according to claim 5, wherein said compression means includes a diaphragm pump.

8. The non-contact tonometer according to claim 5, wherein said compression means includes a piston pump.

9. The non-contact tonometer according to claim 1, wherein said motor is a linear motor.

10. The non-contact tonometer according to claim 9, wherein said linear motor includes a permanent magnet connected to said compression means and axially movable relative to a fixed coil.

11. The non-contact tonometer according to claim 9, wherein said linear motor includes a coil connected to said compression means and axially movable relative to a fixed permanent magnet.

12. The non-contact tonometer according to claim 11, wherein said movable coil is a voice coil.

13. The non-contact tonometer according to claim 9, wherein said linear motor includes a coil connected to said compression means and axially movable relative to a fixed electromagnet.

14. The non-contact tonometer according to claim 13, wherein said movable coil is a voice coil.

15. The non-contact tonometer according to claim 14, wherein said compression means includes a diaphragm pump.

16. The non-contact tonometer according to claim 9, wherein said compression means includes a bellows pump.

17. The non-contact tonometer according to claim 9, wherein said compression means includes a diaphragm pump.

18. The non-contact tonometer according to claim 9, wherein said compression means includes a piston pump.

19. A non-contact tonometer for making a measurement of intraocular pressure of an eye, said non-contact tonometer having an outlet for directing an increasing velocity air pulse toward said eye and detecting means for generating a signal indicating applanation of the eye caused by said air pulse, which comprises:

compression means communicating with said outlet for generating said air pulse;

a linear motor drivably connected to said compression means;

energizing means connected to said linear motor for providing force to move said compression means in a first direction along an axis and produce said air pulse; and short circuit means for disconnecting said energizing means from said motor directly in response to said signal generated during said measurement.

\* \* \* \* \*